US00PP17943P2

(12) United States Plant Patent
Jandrew

(10) Patent No.: US PP17,943 P2
(45) Date of Patent: Aug. 21, 2007

(54) ***SCAEVOLA* PLANT NAMED 'BOMY PINKA'**

(50) Latin Name: *Scaevola aemula*
Varietal Denomination: Bomy Pinka

(75) Inventor: Jason Jandrew, Gilroy, CA (US)

(73) Assignee: Goldsmith Seeds, Inc., Gilroy, CA (US)

( * ) Notice: Subject to any disclaimer, the term of this patent is extended or adjusted under 35 U.S.C. 154(b) by 0 days.

(21) Appl. No.: 11/386,620

(22) Filed: Mar. 22, 2006

(51) Int. Cl.
*A01H 5/00* (2006.01)

(52) U.S. Cl. ..... Plt./363

(58) Field of Classification Search ..... Plt./363
See application file for complete search history.

*Primary Examiner*—Kent Bell
(74) *Attorney, Agent, or Firm*—Jondle & Associates P.C.

(57) ABSTRACT

A *Scaevola* plant particularly distinguished by light pink flowers in a tight cluster, a mid-season and continuous flowering response, medium green foliage with fleshy leaves, a vigorous growth habit and a medium-sized plant habit, an initially spreading to decumbent to trailing plant habit, a rounded, bushy and well-branched plant habit, and good heat tolerance, is disclosed.

2 Drawing Sheets

Genus and species: *Scaevola aemula.*
Variety denomination: 'Bomy Pinka'.

BACKGROUND OF THE NEW PLANT

The present invention comprises a new and distinct cultivar of *Scaevola,* botanically known as *Scaevola aemula* and hereinafter referred to by the cultivar name 'Bomy Pinka'. The new cultivar originated from a hybridization made in July 2003 in Gilroy, Calif. The female parent was '1012', a proprietary violet-flowered *Scaevola* plant (unpatented), while the male parent was '1035', a proprietary violet-blue-flowered *Scaevola* plant (unpatented).

The new cultivar was created in July 2003 in Gilroy, Calif. and has been asexually reproduced repeatedly by vegetative cuttings and tissue culture in Gilroy, Calif. Andijk, The Netherlands and Hillscheid, Germany over a one and one-half-year period. The plant has also been trialed at Gilroy, Calif., Andijk, The Netherlands and Hillscheid, Germany. The present invention has been found to retain its distinctive characteristics through successive asexual propagations.

Plants Breeder's Rights for this cultivar have been applied for in Canada on Mar. 29, 2005.

SUMMARY OF THE INVENTION

The following are the most outstanding and distinguishing characteristics of the new cultivar when grown under normal horticultural practices in Gilroy, Calif. and Hillscheid, Germany.

1. Light pink flowers in a tight cluster;
2. A mid-season and continuous flowering response;
3. Medium green foliage with fleshy leaves;
4. A vigorous growth habit and a medium-sized plant habit;
5. An initially spreading to decumbent to trailing plant habit;
6. A rounded, bushy and well-branched plant habit; and
7. Good heat tolerance.

DESCRIPTION OF THE PHOTOGRAPHS

This new *Scaevola* plant is illustrated by the accompanying photographs which show overall plant habit including inflorescences, buds and foliage of the plant; the colors shown are as true as can be reasonably obtained by conventional photographic procedures. The photos are of a 26-week-old plant grown in a greenhouse in an early September trial setting.

DESCRIPTION OF THE NEW CULTIVAR

Figure 1:
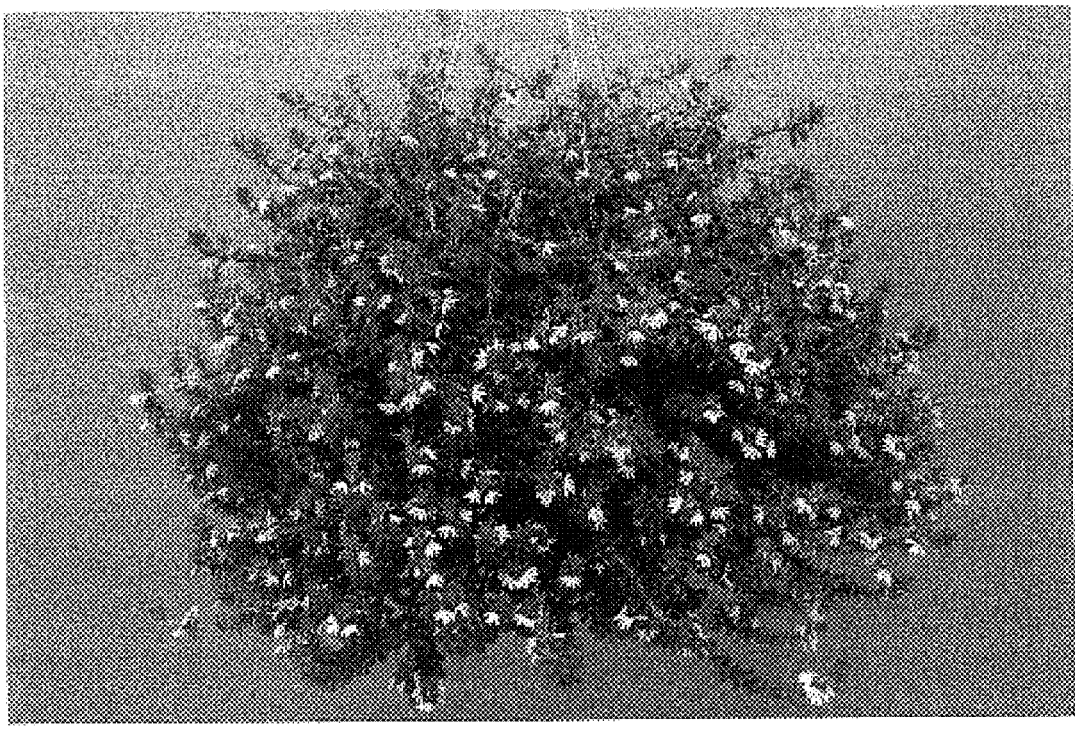
FIG. 1 shows the overall plant habit in a hanging basket, including blooms, buds and foliage.
Figure 2:
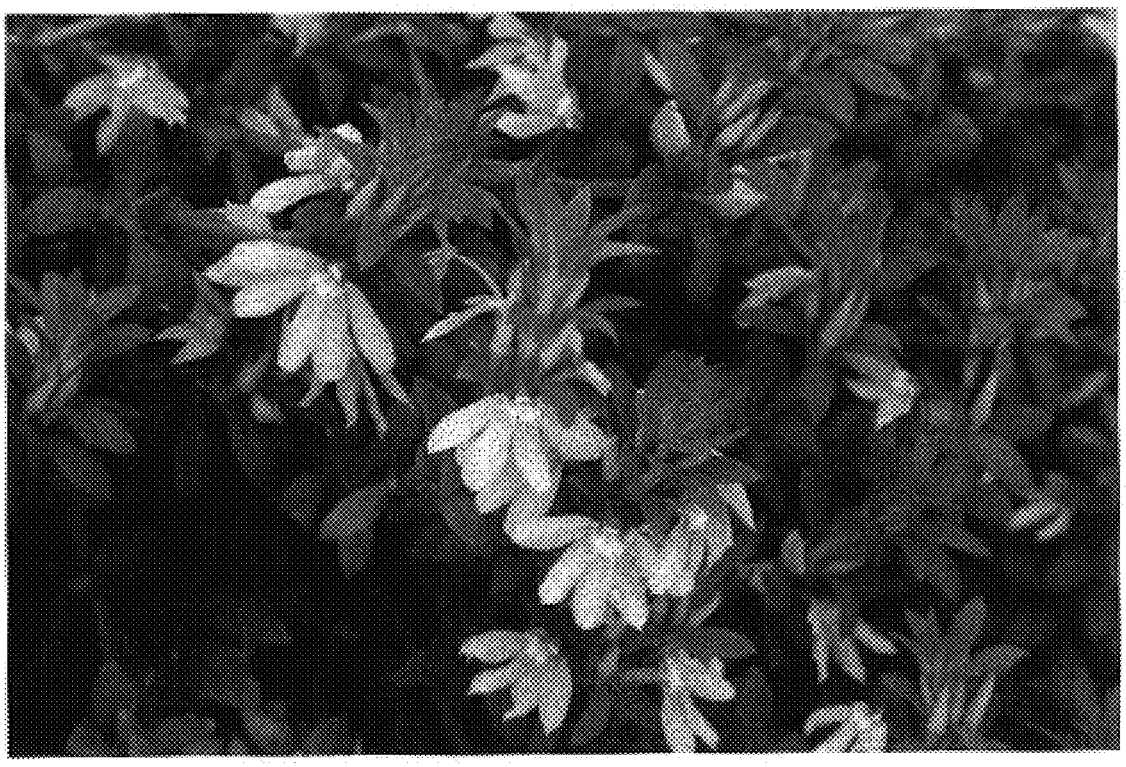
FIG. 2 shows a closer view of a portion of the plant.

The following detailed descriptions set forth the distinctive characteristics of 'Bomy Pinka'. the data which define these characteristics were collected from asexual reproductions carried out in Hillscheid, Germany. Rooted cuttings wee planted into 12-cm plastic pots in early March and pinched once. In late May, the plants were transplanted to outdoor hanging baskets that were situated under light rain protection. The plant history was taken on 11-week-old plants grown in a greenhouse and on 26-week-old plants grown outdoors in Hillscheid, Germany in Spring to late-Summer 2005. Observations were made in mid-May 2005, when the plants began flowering, and then in early September 2005, when the plants were in full-flower and reached their full size. Color readings were taken under natural light. Color references are primarily to the R.H.S. Colour Chart of The Royal Horticultural Society of London (R.H.S.) (2001 edition).

DETAILED BOTANICAL DESCRIPTION

Classification:
*Family.*—Goodeniaceae.
*Botanical.*—*Scaevola aemula.*
*Common name.*—Fan flower.

Parentage:

*Female parent.*—'1012' a proprietary (unpatented) violet-flowered *Scaevola* plant.

*Male parent.*—'1035', a proprietary (unpatented) violet-blue-flowered *Scaevola* plant.

Growth:

*Form.*—Herbaceous perennial.

*Growth and branching habit.*—Initially spreading and later decumbent to trailing; pinching enhances formation of the branches.

*Height* (*measured from the top of the soill ).*—10.5 cm for an 11-week-old plant.

*Width* (*horizontal plant diameter*).—32 cm for an 11-week-old plant

*Plant spread* (*from the base to the shoot tips, including the flowers*).—78 cm for a 26-week-old plant.

*Time to produce a finished flowering plant.*—12 to 14 weeks for a 12-cm pot in the Spring.

*Outdoor plant performance.*—Use in containers and hanging baskets.

*Time to initiate and develop roots.*—About 25 days.

*Root description.*—Fibrous and self-branching.

Stems:

*Number of branches per plant.*—12 to 14.

*Length.*—23 cm for an 11-week-old plant.

*Diameter* (*measured from the midpoint*).—0.3 cm.

*Internode length.*—2 cm to 5 cm.

*Color.*—Mainly RHS 137C and infused with anthocyanin, RHS 177A or lighter, near the tips.

*Texture.*—Glabrous.

Leaves:

*Arrangement.*—Alternate, simple leaves.

*Immature leaf.*—Color: Upper surface: RHS 137B (green); may show RHS 177A anthocyanin at the tips. Lower surface: Near RHS 143B; may show RHS 177A anthocyanin at the tips.

*Mature leaf.*—Color: Upper surface: RHS 137B (green). Lower surface: Between RHS 137D and RHS 143A. Length: 6.5 cm to 7.5 cm for young plants; later about 3.0 cm to 4.0 cm; 1.5 cm on the flowering stems. Width: For young plants, up to 2.5 cm to 1.5 cm for flowering plants; 0.6 cm at the flowering stem tips. Shape: Spatulate, distinctly dentate and later elliptic with no to weak lobing; the leaves of the flowering branches are reflexed and somewhat fleshy and cover the stems in a partly overlapping arrangement resembling scales. Apex: Obtuse to acute. Base: Attenuate. Margin: Initially dentate and later with only a few weak lobes or entire. Texture: Pilose for both upper and lower surfaces. Venation: The midrib is longitudinal and protrudes on the lower surface; other veins are indistinct elsewhere. Venation color: RHS 144A for the lower surface and indistinct for the upper surface.

*Petioles.*—Not clearly distinct from the base of the leaf.

Flower buds:

*Shape.*—Lanceolate and narrow.

*Length.*—2.2 cm.

*Diameter.*—0.4 cm.

*Color* (*at tight bud*).—RHS N182C (brownish-pink) with RHS 187B darker stripes.

Inflorescence:

*Blooming habit.*—Continuously from the Spring through late Summer; flowers appear about 11 to 12 weeks after planting rooted cuttings.

*Lastingness of individual blooms on the plant.*—About 6 to 8 days.

*Fragrance.*—None.

*Inflorescence type.*—Solitary flowers arise from the leaf axils with one flower per leaf axial in an alternate arrangement; 3 to 7 open flowers appear in a cluster and close to the stem tips.

*Flower type.*—Composed of 5 petals slanting upward and fused at the base and in a fan-shaped arrangement to form a lower part which is open tube-shaped.

*Pedicels.*—None, flowers are sessile.

Flowers:

*Flower diameter.*—3.1 cm.

*Flower depth.*—1.8 cm.

*Flower tube.*—Shape: Open tube. Tube length: 1.2 cm to 1.4 cm. Tube diameter (at the opening): 0.5 cm.

*Petals.*—Shape: Elliptic. Apex: Round to acuminate. Base: Fused. Margin: Entire. Texture: Smooth. Color: Immature: Upper surface: RHS 65A to RHS 67D at the base. Lower surface: RHS 65A to RHS 65B. Mature: Upper surface: Mainly RHS 65A (light bluish-pink); RHS 65B near the tips; occasionally with RHS 67D (deeper pink) lines or stripes; a small area of RHS 150D (whitish) at the base. Lower surface: RHS 65B with a weak RHS 182B (brownish) stripe.

Throat color.—Inner surface: RHS N144B (ochre/greenish-yellow) and RHS 183D (brown) lines along the margin. Color outside: RHS N144A and RHS 183C dark lines at the margins.

*Sepals.*—General: Composed of one large sepal and two smaller pin-like sepals. Shape: Lanceolate for the larger sepal and narrow subulate for the two smaller sepals. Apex: Acute, pointed. Base: Sessile. Margin: Entire. Texture: Thin pubescence. Color: RHS 143A for both the upper and lower surfaces. Length: 1.0 cm to 1.5 cm. Width: 0.2 cm to 0.5 cm.

Reproductive organs:

*Stamen.*—Quantity: 5, protruding from the flower throat. Anther shape: Narrowly ovate. Anther length: 0.3 cm. Anther color: RHS 151 (yellowish). Filament color: RHS 155D (whitish). Filament diameter: 0.1 cm. Filament length: 0.3 cm. Pollen amount: Sparse. Pollen color: RHS 4D (yellow-white).

*Pistil.*—Quantity: 1. Pistil length: 1.5 cm. Style diameter: 0.4 cm at the tip. Style color: RHS 183B. Stigma color: RHS 150D (whitish).

Fruit/seed set: None observed.

Disease and insect resistance: No special observations made.

COMPARISON WITH PARENTAL AND COMMERCIAL CULTIVARS

'Bomy Pinka' differs from the female parent '1012' (unpatented), in that 'Bomy Pinka' has light pink flowers, while '1012' has violet flowers. Additionally, 'Bomy Pinka' has an earlier flowering response and a more compact plant habit than '1012'.

'Bomy Pinka' differs from the male parent '1035' (unpatented), in that 'Bomy Pinka' has light pink flowers, while '1035' has violet-blue flowers. Additionally, 'Bomy Pinka' has larger flowers and lighter green foliage than '1035'.

'Bomy Pinka' differs from the variety 'Bomy Blue' (U.S. Plant patent application Ser. No. 11/386,557), in that the leaves of 'Bomy Pink' are spatulate, distinctly dentate and later elliptic with no to weak lobing, while the leaves of 'Bomy Bule' are oblanceolate and spatulate with distinct dentation. Additionally, 'Bomy Pinka' has a smaller plant habit than 'Bomy Blue'.

'Bomy Pinka' differs from the variety 'Bomy Litbule' (U.S. Plant patent application Ser. No. 11/386,621) primarily in flower color.

'Bomy Pinka' differs from the commercial variety 'Pink Fanfare' (Patent status unknown), in that 'Bomy Pinka' develops fewer basal branches and longer internodes than 'Pink Fanfare'. Additionally, 'Bomy Pinka' has wider leaves than 'Pink Fanfare'.

I claim:

1. A new and distinct cultivar of *Scaevola* plant as shown and described herein.

* * * * *